(12) United States Patent
Gellman

(10) Patent No.: US 6,689,047 B2
(45) Date of Patent: Feb. 10, 2004

(54) TREATING URINARY INCONTINENCE

(75) Inventor: Barry N. Gellman, North Easton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 203 days.

(21) Appl. No.: 09/992,359

(22) Filed: Nov. 14, 2001

(65) Prior Publication Data

US 2002/0058959 A1 May 16, 2002

Related U.S. Application Data

(60) Provisional application No. 60/248,808, filed on Nov. 15, 2000.

(51) Int. Cl.$^7$ .............................. A61F 2/02; A61F 2/00; A61B 17/04
(52) U.S. Cl. ................. 600/30; 606/148; 128/DIG. 25; 600/37
(58) Field of Search ............................... 600/29–30, 37; 606/148, 167, 144–146, 139, 198, 196, 205–209, 119, 118, 138, 140, 141, 222–228, 72–75; 128/DIG. 25; 60/119; 28/897, 898; 604/515

(56) References Cited

U.S. PATENT DOCUMENTS

| | | |
|---|---|---|
| 2,671,444 A | 3/1954 | Pease |
| 3,054,406 A | 9/1962 | Usher |
| 3,124,136 A | 3/1964 | Usher |
| 3,364,200 A | 1/1968 | Ashton et al. |
| 3,580,313 A | 5/1971 | McKnight |
| 3,666,750 A | 5/1972 | Briskin et al. |
| 3,705,575 A | 12/1972 | Edwards |
| 3,744,495 A | 7/1973 | Johnson |
| 3,823,705 A | 7/1974 | Trimble |
| 4,085,756 A | 4/1978 | Weaver |
| 4,172,458 A | 10/1979 | Pereyra |
| 4,175,557 A | 11/1979 | Hung |
| 4,193,137 A | 3/1980 | Heck |
| 4,347,847 A | 9/1982 | Usher |
| 4,400,833 A | 8/1983 | Kurland |
| 4,409,974 A | 10/1983 | Freedland |
| 4,414,967 A | 11/1983 | Shapiro |
| 4,452,245 A | 6/1984 | Usher |
| 4,520,821 A | 6/1985 | Schmidt et al. |
| 4,545,374 A | 10/1985 | Jacobson |
| 4,549,545 A | 10/1985 | Levy |
| 4,633,873 A | 1/1987 | Dumican et al. |
| 4,652,264 A | 3/1987 | Dumican |

(List continued on next page.)

FOREIGN PATENT DOCUMENTS

| | | |
|---|---|---|
| DE | 43 23 578 A1 | 1/1994 |
| EP | 0 417 031 A2 | 3/1991 |

(List continued on next page.)

OTHER PUBLICATIONS

Vasavada et al., Incisionless Pubovaginal Fascial Sling Using Transvaginal Bone Anchors for the Treatment of Stress Urinary Incontinence, Digital Urology Journal, Jul. 24, 2001.

Urken, About our LifeCell Our Science, LifeCell, Jul. 24, 2001.

(List continued on next page.)

*Primary Examiner*—Eric F. Winakur
*Assistant Examiner*—Nikita R Veniaminov
(74) *Attorney, Agent, or Firm*—Testa, Hurwitz & Thibeault, LLP.

(57) ABSTRACT

A surgical device for use in a minimally invasive procedure to treat urinary incontinence can include a dilator coupled to a curved needle at one end and a sling at the opposite end. Urinary incontinence can be treated minimally invasively. One treatment includes positioning the sling on an anterior portion of the urethra to provide proper coaptation to the urethra.

23 Claims, 3 Drawing Sheets

U.S. PATENT DOCUMENTS

| | | |
|---|---|---|
| 4,655,221 A | 4/1987 | Devereux |
| 4,741,330 A | 5/1988 | Hayhurst |
| 4,769,038 A | 9/1988 | Bendavid et al. |
| 4,784,126 A | 11/1988 | Hourahane |
| 4,838,884 A | 6/1989 | Dumican et al. |
| 4,854,316 A | 8/1989 | Davis |
| 4,857,041 A | 8/1989 | Annis et al. |
| 4,872,451 A | 10/1989 | Moore et al. |
| 4,873,977 A | 10/1989 | Avant et al. |
| 4,905,692 A | 3/1990 | More |
| 4,911,165 A | 3/1990 | Lennard et al. |
| 4,938,760 A | 7/1990 | Burton et al. |
| 4,969,892 A | 11/1990 | Burton et al. |
| 4,973,300 A | 11/1990 | Wright |
| 4,986,831 A | 1/1991 | King et al. |
| 4,997,434 A | 3/1991 | Seedhom et al. |
| 5,002,551 A | 3/1991 | Linsky et al. |
| 5,012,822 A | 5/1991 | Schwarz |
| 5,013,292 A | 5/1991 | Lemay |
| 5,019,032 A | 5/1991 | Robertson |
| 5,026,398 A | 6/1991 | May |
| 5,064,434 A | 11/1991 | Haber |
| 5,112,344 A | 5/1992 | Petros |
| 5,122,155 A | 6/1992 | Eberbach |
| 5,147,374 A | 9/1992 | Fernandez |
| 5,149,329 A | 9/1992 | Richardson |
| 5,176,692 A | 1/1993 | Wilk et al. |
| 5,178,630 A | 1/1993 | Schmitt |
| 5,195,542 A | 3/1993 | Gazielly et al. |
| 5,254,133 A | 10/1993 | Seid |
| 5,256,133 A | 10/1993 | Spitz |
| 5,258,000 A | 11/1993 | Gianturco |
| 5,263,969 A | 11/1993 | Phillips |
| 5,289,963 A | 3/1994 | McGarry et al. |
| 5,290,217 A | 3/1994 | Campos |
| 5,292,328 A | 3/1994 | Hain et al. |
| 5,304,220 A | 4/1994 | Maginot |
| 5,328,077 A | 7/1994 | Lou |
| 5,337,736 A | 8/1994 | Reddy |
| 5,354,292 A | 10/1994 | Braeuer et al. |
| 5,356,064 A | 10/1994 | Green et al. |
| 5,362,294 A | 11/1994 | Seitzinger |
| 5,364,002 A | 11/1994 | Green et al. |
| 5,366,460 A | 11/1994 | Eberbach |
| 5,366,479 A | 11/1994 | McGarry et al. |
| 5,368,602 A | 11/1994 | de la Torre |
| 5,370,650 A | 12/1994 | Tovey et al. |
| 5,381,943 A | 1/1995 | Allen et al. |
| 5,383,477 A | 1/1995 | DeMatteis |
| 5,397,332 A | 3/1995 | Kammerer et al. |
| 5,425,737 A | 6/1995 | Burbank et al. |
| 5,425,984 A | 6/1995 | Kennedy et al. |
| 5,431,173 A | 7/1995 | Chin |
| 5,437,603 A | 8/1995 | Cerny et al. |
| 5,441,508 A | 8/1995 | Gazielly |
| 5,451,235 A | 9/1995 | Lock et al. |
| 5,474,543 A | 12/1995 | McKay |
| 5,507,796 A | 4/1996 | Hasson |
| 5,527,341 A | 6/1996 | Gogolewski et al. |
| 5,527,342 A | 6/1996 | Pietrzak et al. |
| 5,544,664 A | 8/1996 | Benderev et al. |
| 5,549,619 A | 8/1996 | Peters et al. |
| 5,569,273 A | 10/1996 | Titone et al. |
| 5,582,188 A | 12/1996 | Benderev et al. |
| 5,591,163 A | 1/1997 | Thompson |
| 5,611,515 A | 3/1997 | Benderev et al. |
| 5,620,012 A | 4/1997 | Benderev et al. |
| 5,634,931 A | 6/1997 | Kugel |
| 5,634,944 A | 6/1997 | Magram |
| 5,641,502 A | 6/1997 | Skalla et al. |
| 5,641,566 A | 6/1997 | Kranzler et al. |
| 5,643,288 A | 7/1997 | Thompson |
| 5,643,596 A | 7/1997 | Pruss et al. |
| 5,645,849 A | 7/1997 | Pruss et al. |
| 5,645,915 A | 7/1997 | Kranzler et al. |
| 5,681,310 A | 10/1997 | Yuan et al. |
| 5,690,655 A | 11/1997 | Hart et al. |
| 5,697,931 A | 12/1997 | Thompson |
| 5,707,647 A | 1/1998 | Dunn et al. |
| 5,733,337 A | 3/1998 | Carr, Jr. et al. |
| 5,766,221 A | 6/1998 | Benderev et al. |
| 5,769,864 A | 6/1998 | Kugel |
| 5,807,403 A | 9/1998 | Beyar et al. |
| 5,816,258 A | 10/1998 | Jervis |
| 5,836,314 A | 11/1998 | Benderev et al. |
| 5,836,315 A | 11/1998 | Benderev et al. |
| 5,836,961 A | 11/1998 | Kieturakis et al. |
| 5,840,011 A | 11/1998 | Landgrebe et al. |
| 5,899,909 A | 5/1999 | Claren et al. |
| 5,916,225 A | 6/1999 | Kugel |
| 5,922,026 A | 7/1999 | Chin |
| 5,934,283 A | 8/1999 | Willem et al. |
| 5,997,554 A | 12/1999 | Thompson |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,053,935 A | 4/2000 | Brenneman et al. |
| 6,059,801 A | 5/2000 | Samimi |
| 6,068,591 A | 5/2000 | Bruckner et al. |
| 6,090,116 A | 7/2000 | D'Aversa et al. |
| 6,096,051 A * | 8/2000 | Kortenbach et al. ........ 606/144 |
| 6,099,547 A | 8/2000 | Gellman et al. |
| 6,102,921 A | 8/2000 | Zhu et al. |
| 6,110,101 A | 8/2000 | Tihon et al. |
| 6,221,005 B1 | 4/2001 | Bruckner et al. |
| 6,273,852 B1 * | 8/2001 | Lehe et al. .................... 600/30 |
| 6,423,080 B1 * | 7/2002 | Gellman et al. ............ 606/148 |
| 6,454,778 B2 * | 9/2002 | Kortenbach .................. 606/144 |
| 6,478,727 B2 * | 11/2002 | Scetbon ....................... 600/30 |
| 2002/0055748 A1 * | 5/2002 | Gellman et al. ............ 606/139 |

FOREIGN PATENT DOCUMENTS

| | | |
|---|---|---|
| EP | 0 599 772 A | 6/1994 |
| EP | 0 334 046 B1 | 6/1997 |
| EP | 0 778 749 B1 | 12/2000 |
| GB | 2 268 690 | 1/1994 |
| GB | 2268690 | 1/1994 |
| JP | 6-114067 | 4/1994 |
| SE | 503 271 | 3/1996 |
| SE | 506 164 | 4/1997 |
| WO | 88/01853 | 3/1988 |
| WO | 92/16152 | 10/1992 |
| WO | 93/10715 | 6/1993 |
| WO | 93/10731 | 6/1993 |
| WO | 93/19678 | 10/1993 |
| WO | 94/19029 | 1/1994 |
| WO | 94/28799 | 12/1994 |
| WO | 96/06567 | 3/1996 |
| WO | 97/13465 | 4/1997 |
| WO | 97/30638 | 8/1997 |
| WO | 97/41792 | 11/1997 |
| WO | 97/43982 | 11/1997 |
| WO | 98/12971 | 4/1998 |
| WO | 98/35616 | 8/1998 |
| WO | 98/35632 | 8/1998 |
| WO | 00/74633 A2 | 12/2000 |

OTHER PUBLICATIONS

Kovac: Pubic Bone Suburethral Stabilization Sling for Recurrent Urinary Incontinence, Obstetrics and Gynecology 89:624–627 (1997).

Iglesia et al., "The Use of Mesh in Gynecologic Surgery", 8:105–115 (1997).

Cruikshank: Anterior vaginal wall culdeplasty at vaginal hysterectomy to prevent posthysterectomy anterior vaginal wall prolapse, Am. J. Obstetrics and Gynecology 174: 1863–1872 (1996).

Leach: Percutaneous Bladder Neck Suspension, Urol Clinics of N. Am. 23: 511–516 (1996).

Petros et al., The Intravaginal Slingplasty Operation, a Minimally Invasive Technique for Cure of Urinary Incontinence in the Female, Aust. NZ 1. Obstet. Gynaecol. 36: 453–461 (1996).

Hoffman: Transvestibular Retropubic Bladder Neck Suspension: A pilot study, J. Reproductive Med. 40: 181–184 (1995).

Trockman: Modified Pereyra Bladder Neck Suspension: 10–year mean follow–up using outcomes analysis in 125 patients, J. Urology 154: 1841–1847 (1995).

Ulmsten: Intravaginal Slingplasty (IVS): An Ambulatory Surgical Procedure for Treatment of Female Urinary Incontinence Scand. J. Urol. Nephrol 29: 75–82, (1995).

DeLancey, "Structural Support of the Urethra as it Relates to Stress Urinary Incontinence: The Hammock Hypothesis", *Am. J. Obstet Gynecol*, 170:1713–1723, 1994.

Blaivas et al., "Successful Pubovaginal Sling Surgery", *Contemporary Urology*, pp. 40–63, Jul. 1993.

Blaivas et al., "Pubovaginal Fascial Sling for the Treatment of Complicated Stress Urinary Incontinence", *The Journal of Urology*, vol. 145, pp. 1214–1218, Jun. 1991.

Zimmern: A prospective evaluation of Four–Corner bladder neck suspension for Grade 11/111 Cystocele repair, Neurol. and Urodynamics 9: 231 (1990).

Leach: Bone fixation technique for transvaginal needle suspension, Urology 31: 388–390 (1988).

Gittes: No–incision pubovaginal suspension for stress incontinence, J. Urology 138: 568–570 (1987).

Spencer: A comparison of Endoscopic suspension of the vesical neck with suprapubic vesicourethropexy for treatment of stress urinary incontinence, J. Urology 137: 411–415 (1987).

Bayer: A new apporach to primary strengthening of colostomy with Marlex® Mesh to prevent paracolostomy hernia, Surgery, Gynecology and Obstetrics 163: 579–580 (1986).

Stamey: "Endoscopic Suspension of the Vesical Neck", *Surgery of Female Incontinence*, 115–132, 1986.

Zimmern: Trasvaginal Colsure of the Bladder Neck, Seminars in Urology 4: 30–32 (1986).

Forneret: Cost–effective treatment of female stress urinary incontinence: modified pereyra bladder neck suspension, Urology 25: 365–367 (1985).

Zacharin, "Abdominoperineal Urethral Suspension in the Management of Recurrent Stress Incontinence of Urine—a 15–year Experience", *Obstetrics & Gynecology*, vol. 62, No. 5, (Nov. 1983).

Webster: "Female Urinary Incontinence," *Urologic Surgery*, J.B. Lippincott Company: Philadelphia, 665–679, 1983.

Winter: Peripubic urethropexy for urinary stress incontinecne in women, Urology 20: 408–411 (1982).

Richardson et al., "Treatment of Stress Urinary Incontinence Due to Paravaginal Fascial Defect", Obstetrics & Gynecology, vol. 57, No. 3, (Mar. 1981).

Hancock: Transpubic suspension of the Bladder Neck for Urinary Incontinence, J. Urology 123: 667–668 (1980).

Stamey: Endoscopic Suspension of the Vesical Neck for Urinary Incontinence in Females: Report on 203 Consecutive patients, Ann. Surg. 192: 465–471 (1980).

Nichols et al., "Identification of Pubourethral Ligaments and Their Role in Transvaginal Surgical Correction of Stress Incontinence", *Am. J. Obstet. Gynecol.*, vol. 115, No. 1, Jan. 1, 1973.

Stamey: Endoscopic Suspension of the vesical neck for urinary incontinence, Surgery, Gynecology and Obstetrics 136: 547–554 (1973).

McKiel: Marshall–Marchetti Procedure: Modification, J. Urology 96: 737–739 (1966).

McGuire: The Sling Procedure for Urinary Stress Incontinence, Profiles in Urology—The Sling Procedure for Urinary Stress Incontinence.

* cited by examiner

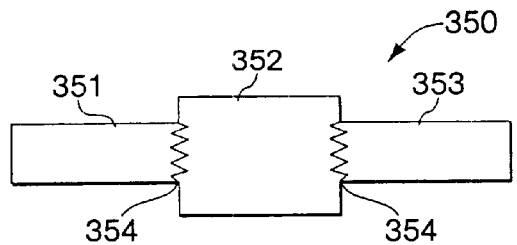
Fig. 5
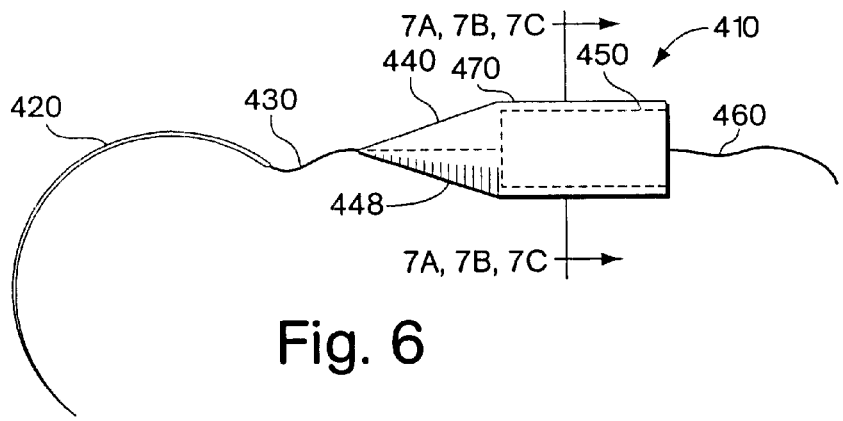
Fig. 6
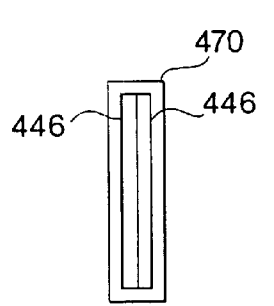 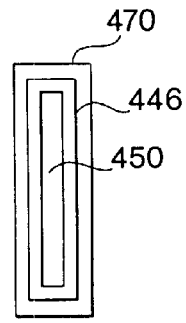 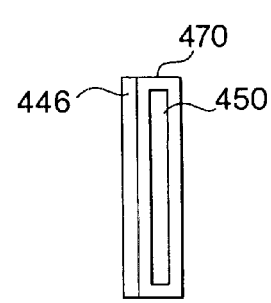
Fig. 7A    Fig. 7B    Fig. 7C
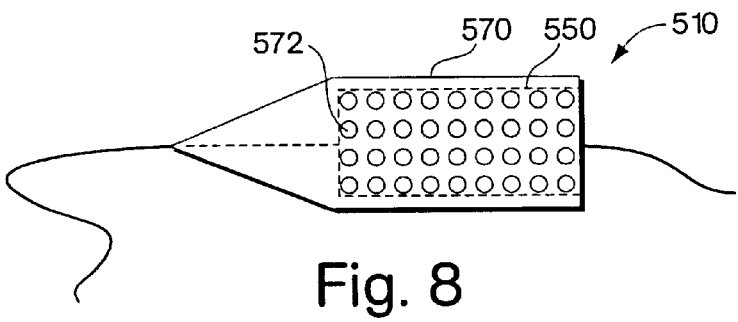
Fig. 8

TREATING URINARY INCONTINENCE

CROSS-REFERENCE TO RELATED CASE

This application claims priority to U.S. provisional patent application Serial No. 60/248,808 filed on Nov. 15, 2000, which is incorporated herein by reference in its entirety.

TECHNICAL FIELD

The present invention relates to devices and methods for treating urinary incontinence, such as urinary incontinence in women resulting from intrinsic sphincter deficiency.

BACKGROUND INFORMATION

Urinary incontinence is a widespread problem throughout the world. Urinary incontinence affects people of all ages and can severely impact a patient both physiologically and psychologically.

One form of urinary incontinence suffered by women is intrinsic sphincter deficiency (ISD), a condition in which the valve of the urethral sphincter does not function properly, thus preventing proper coaptation of the urethra. Without proper coaptation, a person is unable to control urinary leakage. ISD can arise from loss of urethral vasculature, thinning of urethral mucosa, loss of the urethral connective tissue elements, neurologic compromise of the sympathetic smooth muscle, or compromise of the external striated sphincter.

Another form of urinary incontinence is known as bladder neck hypermobility. Bladder neck hypermobility can arise from loss of support by the pelvic floor and loss of suspension by the pelvic connective tissue in ligaments and fascia. In this condition, the bladder neck and proximal urethra descend in response to increases in intra-abdominal pressure, resulting in uncontrollable urinary leakage.

Common approaches to treating urinary incontinence in women require invasive surgical procedures either through the vaginal wall or the abdominal wall. These surgical procedures focus on elevating the urethrovesical junction by introducing a sling that passes to the posterior side of the urethra and suspending the urethra from an anatomical structure located anterior to the urethra, for example, the abdominal fascia, the pubic bone, or the Cooper's ligament. Surgical treatments of urinary incontinence that use slings typically involve placing the sling under the urethra to provide suburethral support. Slings of this type simultaneously compress and suspend the urethra to treat urinary incontinence. One disadvantage of these procedures is the invasive nature of these procedures. Another disadvantage is that weight gain or loss can affect the suspension of the urethra causing it to become too tight or too loose. Still another disadvantage is that some types of slings may shrink with age and may cause difficulties with voiding. Other invasive surgical approaches to treating urinary incontinence include the use of vaginal wall slings and/or artificial urinary sphincters.

Periurethral injection (PI) of biocompatible bulk-enhancing agents, another approach to treating urinary incontinence, has the advantage of being a less invasive form of treatment and, thus, can be performed on an outpatient basis. PI uses bulk-enhancing agents, such as Teflon® (DuPont), autologous fat, and collagen, to increase pressure on the urethra and reduce the size of the urethral lumen, providing additional resistance to the flow of urine. Such injections may be accomplished either transurethrally or periurethrally. Typically, however, repeat treatments of PI are required because the bulk-enhancing agent can be absorbed by the body or translocated from the site of injection. Another drawback to PI is that accidental over-bulking may result in undesirable urinary retention requiring catheterization to void until the injectant is absorbed by the body.

SUMMARY OF THE INVENTION

The present invention relates to a treatment for urinary incontinence without drawbacks associated with more invasive surgeries or PI. The invention generally involves coapting a urethra externally between a sling and a vaginal wall. The term "urethra," as used herein, generally includes the bladder neck. Because of the minimally invasive nature of the invention, a procedure according to the invention can be performed in conjunction with other transvaginal procedures. In addition, such a procedure can quickly and easily be reversed as the sling may be held in place by removable securing devices such as sutures or surgical staples.

In one aspect, the invention features a surgical device for treating urinary incontinence that includes a curved needle, a dilator, and a sling. A distal end of the dilator is coupled to a proximal end of the curved needle, and a distal end of the sling is coupled to a proximal end of the dilator.

In some embodiments, the curved needle includes a curvature sufficient to allow the needle to enter the body from the vaginal cavity and through the vaginal wall, pass to one side of the urethra, continue over an anterior side of the urethra, and exit the body on the other side of the urethra.

The dilator generally can be any shape in which the distal end is tapered and the proximal end can create an opening to accommodate a sling as it follows the dilator into the body. In some embodiments, the dilator can be substantially flat and triangular in shape. In other embodiments, the dilator can be substantially rectangular and tapered at the distal end. The dilator can be made from one or more biocompatible materials such as a plastic or metal. The dilator can also include markings to indicate the location of the sling within the body.

The sling can be made of one or more biocompatible materials selected from the group consisting of a natural material, a synthetic material, or a combination of a natural material and a synthetic material. The sling can be about 0.5 cm to about 4 cm in width. In a particular embodiment, the sling is about 1 to about 3 cm in width. In another particular embodiment, the sling is about 1.5 to about 2.5 cm in width.

In some embodiments, a tether couples the curved needle to the dilator. Examples of the form the tether may take includes a wire, a suture, and a portion of the sling.

In some embodiments, a first portion of the sling can be smaller in width than a middle portion of the sling. In a particular embodiment, the first portion of the sling can couple the sling to the dilator. In another particular embodiment, the first portion of the sling can couple the dilator to the needle.

In some embodiments, a pouch can be fixedly attached to the dilator and releasably attached to the sling. In other embodiments, the surgical device can include a stiffener to maintain the sling in a generally planar orientation as it enters the body.

In another aspect, the invention features a surgical device that includes a sling, a first tether with a proximal end coupled to a distal end of the sling, a second tether with a distal end coupled to a proximal end of the sling, a curved needle coupled to a distal end of the first tether, and a dilator disposed along the first tether between the curved needle and the distal end of the sling.

In yet another aspect, the invention features a method of treating urinary incontinence. The method includes introducing a sling into a body and positioning the sling on an anterior side of the urethra to coapt the urethra against the vaginal wall. The sling can be introduced into the body via the vaginal cavity and through the vaginal wall. In some embodiments, the sling is positioned to surround less than 360° of the circumference of the urethra. In some embodiments, the sling is positioned to surround approximately 180° of the circumference of the urethra on an anterior side of the urethra. In other embodiments, the sling is positioned to surround approximately 90° to approximately 180° of the urethra on the anterior side of the urethra.

In some embodiments, a surgical device according to the invention is introduced into the body via the vaginal cavity and through the vaginal wall to pass to one side of the urethra, and then pass about the anterior side of the urethra, and to exit the body on the other side of the urethra into the vaginal cavity. The surgical device can include a curved needle, a dilator, and a sling, and the sling can be positioned in the body to coapt the urethra to an anterior portion of the vaginal wall in the body.

In some embodiments, the anterior of the urethra is separated from surrounding tissue, for example, the bladder. The separating step can be performed, for example, by using hydrodissection or balloon dissection.

In still another aspect, the invention features a method of treating urinary incontinence. The method includes introducing a surgical device into a body via the vaginal cavity. The surgical device can comprise a sling, including a distal end and a proximal end, and a first tether, including a distal end and a proximal end, wherein the proximal end of the tether is coupled to a distal end of the sling. The device can also include a second tether, including a distal end and a proximal end, wherein the distal end of the second tether is coupled to a proximal end of the sling. The device can also include a curved needle coupled to the distal end of the first tether and a dilator disposed along the first tether between the curved needle and the distal end of the sling. The curved needle is passed into the body via the vaginal cavity, through the vaginal wall to one side of the urethra, over an anterior portion of the urethra, and out of the body on the other side of the urethra into the vaginal cavity, creating a path for the first tether, the dilator, the sling, and the second tether to follow. The dilator is advanced along the path to position the sling about the urethra, leaving at least a portion of the second tether in the vaginal cavity. The dilator and at least a portion of the first tether exits the body into the vaginal cavity, leaving the sling in place about the anterior portion of the urethra to coapt the urethra to the anterior portion of the vaginal wall. The first tether and second tether are secured to an interior wall of the vaginal cavity.

The method can also include separating the anterior portion of the urethra from the surrounding tissue to create a pocket or opening to accommodate the sling.

These and other objects, along with advantages and features of the invention disclosed herein, will be made more apparent from the description, drawings, and claims that follow.

BRIEF DESCRIPTION OF THE DRAWINGS

In the drawings, like reference characters generally refer to the same parts throughout the different views. Also, the drawings are not necessarily to scale, emphasis instead being placed generally upon illustrating the principles of the invention.

FIG. 5 shows a sling according to one embodiment of the invention.

FIG. 6 shows a surgical device according to one embodiment of the invention.

FIGS. 7A–C show three exemplary embodiments of transverse cross-sectional views of the surgical device of FIG. 6 along section 7A, 7B, 7C—7A, 7B, 7C.

FIG. 8 shows a surgical device according to one embodiment of the invention.

DESCRIPTION

Figure 1:
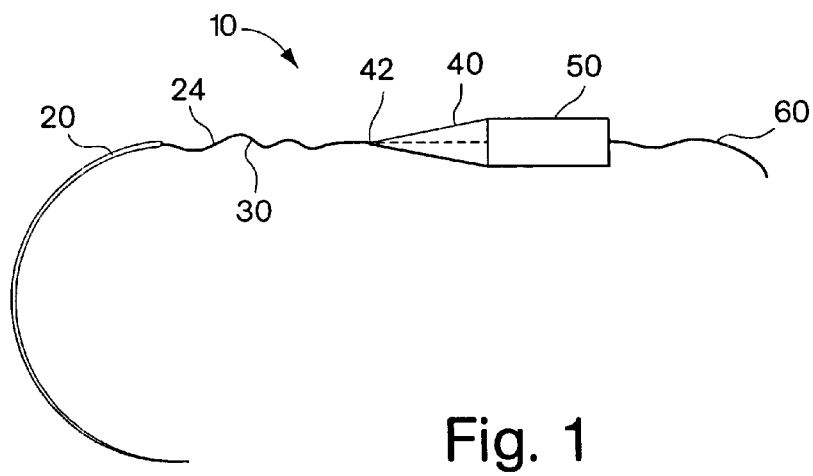
FIG. 1 shows a surgical device according to one embodiment of the invention.

FIG. 1 depicts a surgical device 10 according to one embodiment of the present invention. FIG. 1 shows a curved needle 20, a first tether 30, a dilator 40, a sling 50, and a second tether 60.

The curved needle 20 can be any curved needle used to guide the rest of the surgical device 10 around a bladder neck. The needle 20 can be a curved solid needle, a hollow needle, or a channeled needle. The proximal end of the needle 24 can have an eyelet or other attachment structure. The first tether 30 is shown to couple the dilator 40 to the curved needle 20. The tether 30 can be coupled to the needle 20 by any means including, but not limited to, tying, gluing, looping, crimping, and bonding.

Figure 9:
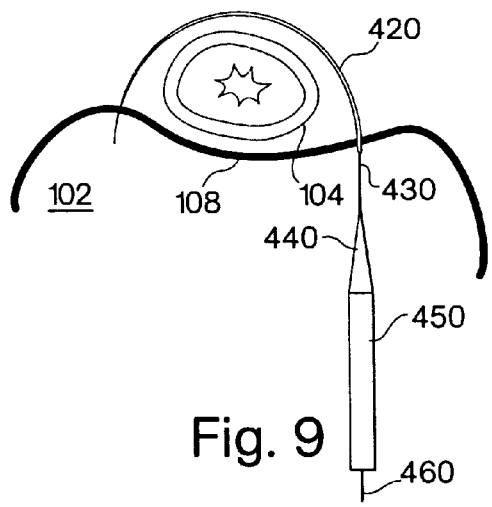
FIG. 9 is a schematic diagram of a step in a method according to one embodiment of the invention.

The curvature of the needle 20 should be sufficient to pass around a urethra 104 from a vaginal cavity 102, as shown in FIG. 9. The needle 20 may be of any size and/or type. For example, the needle 20 may be a ½ circle or a ⅜ circle needle. The needle 20 may be of any point configuration such as a cutting point or a reverse cutting point. The size of the needle 20 may also range from 12 mm-25 mm. Examples of needles 20 include, but are not limited to, Ethicon PC-12 and PS-5. (Ethicon, Inc., Somerville, N.J.)

The first tether 30 and the second tether 60 can be formed from a suture, a wire, a portion of the sling 50, or any other material that is strong enough to resist breaking as the surgical device 10 is passed through the body. The tethers 30, 60 may be attached to the sling 50 in any number of ways known in the art such as tying, suturing, bonding, or molding. The tethers 30, 60 can also be used to secure the sling 50 in place once it is disposed around the urethra 104. The sling 50 is secured by the tethers 30, 60 to the interior portion of the vaginal wall. Typically, the tethers 30, 60 remaining in the vaginal wall will eventually be covered with endothelial tissue. In some embodiments, the tether 30, 60 is a suture. The suture can be a non-absorbable suture such as a polyester, for example Dacron® polyester (DuPont, Wilmington, Del.), an expanded polytetrafluoroethylene (EPTFE), such as Gore-Tex® (W.L. Gore & Associates, Inc., Newark, Del.), a polypropylene, or a braided silk. Other suitable materials that can be used as a suture will be apparent to those skilled in the art.

Figure 10:
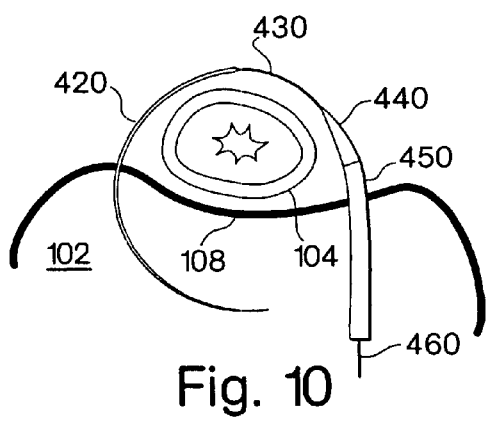
FIG. 10 is a schematic diagram of a step in a method according to one embodiment of the invention.

The dilator 40 can be made of a semi-rigid plastic material. Examples of such materials include, but are not limited to, polyethylene terephthalate (PET), polyethylene (PE), or ethylene vinyl acetate (EVA). The dilator 40 is sufficiently rigid to push through the tissue of the body and create an opening for the sling 50, but also sufficiently flexible to curve axially around the urethra 104, following the path of the curved needle 20, as shown in FIGS. 9 and 10.

The distal end 42 of the dilator 40 can be substantially similar in size to the proximal end 24 of the curved needle 20. From the distal end 42 of the dilator 40, the dilator 40 can expand in a planar direction, a cylindrical direction (i.e., increasing circumference), or combination of both a planar direction and a cylindrical direction. For example, if the dilator 40 expands in a planar direction, the resultant dilator 40 is substantially flat and triangular in shape. The dilator 40 preferably expands until it reaches a size not less than the width of the sling 50, to ensure that the opening created by the dilator 40 will accommodate the width of the sling 50. The dilator 40 can terminate at a maximum width, whereby the passage of the dilator 40 through the body creates an opening sufficiently wide to allow the sling 50 to pass through the body. The length of the dilator 40 can be sufficient to allow the dilator 40 to be grasped with forceps and pulled and/or pushed through the body, if necessary.

Figure 2:
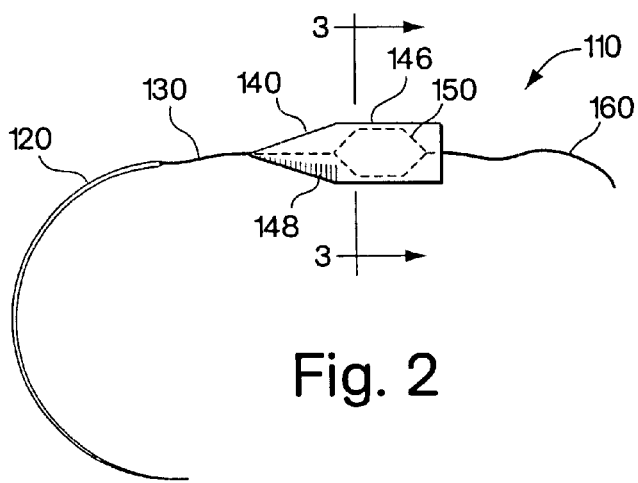
FIG. 2 shows a surgical device according to one embodiment of the invention.
Figure 3:
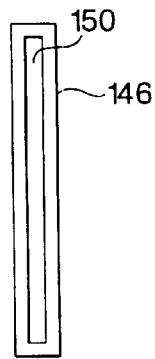
FIG. 3 shows a transverse cross-sectional view of the surgical device of FIG. 2 along section 3—3.

Alternatively, as shown in FIGS. 2 and 3, the dilator 140 can be extended distally to overlap with or partially enclose the sling 150. In embodiments where the dilator 140 is further extended, the proximal portion of the dilator 140 can also be used as a stiffener 146 to prevent the sling 150 from rolling or curling. Alternatively, the stiffener 146 may be a separate element from the dilator 140. The stiffener 146 provides rigidity and prevents distortion of the sling 150 during passage through the patient's body, as well as permitting the dilator 140 to dilate or cut an opening in the patient's body as it passes through the body in the path created by the curved needle 120.

In some embodiments, the curved needle 120 and dilator 140 may be a single unit, for example a curved blade. This single unit may include a sharp point at the distal end to create an incision from which the blade flares out, curving axially along its length, to a maximum width at the proximal end.

The dilator 140 and/or the stiffener 146 may also provide a bending effect that permits the sling 150 to follow an axial bend along its length. Finally, the dilator 140 and the stiffener 146 can reduce damage to the sling 150 during handling.

The stiffener 146 may be made of the same material or a different material than the dilator 140. The stiffener 146 may be made of any of a variety of materials compatible with the above-described considerations including, but not limited to, polyethylene, polypropylene, and acrylic. The stiffener 146 may provide approximately 1 cm radius of bending to 2 cm radius of bending. The stiffener 146 may be porous to permit a solution to access the sling 150 during a soak with a solution. Examples of such materials include, but are not limited to, polyethylene and polyethylene terephthalate made porous by methods well known in the art. Other suitable materials will be apparent to those skilled in the art. The dilator 140 and the stiffener 146 may be adapted to releasably engage the sling 150.

The dilator 140 may also be marked to indicate the position of the sling 150 in the body. The marking(s) 148 are placed along at least a portion of the length of the dilator 140. In this manner, as the surgical device 110 is passed through the body, the user can determine the location of the sling 150 in the body by referring to the markings 148 on the dilator 140.

Figure 4:
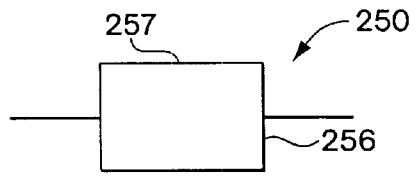
FIG. 4 shows a sling according to one embodiment of the invention.

Referring to FIG. 4, the sling 250 can be made of any biologically acceptable material for implantation into a body. The material can be a supple material that is sterile, or can be effectively sterilized, and is otherwise biologically acceptable for implantation into a body. For example, the material can be a synthetic polymer, a processed animal tissue, or a combination of synthetic polymers and animal tissue. The term "processed animal tissue" means tissue from an animal source, wherein antigenic sites within the tissue are bound, destroyed, or removed so as to reduce the antigenicity of the tissue. Slings are also described in U.S. Pat. No. 6,042,534 issued Mar. 28, 2000, the entire disclosure of which is incorporated herein by reference.

Where the material is processed animal tissue, the tissue can include, among others, porcine tissue, bovine tissue, ovine tissue, equine tissue, and human tissue. Human tissue can be obtained from human cadavers or living donors. Processed animal tissue can be made from tendons, ligaments, and fibro-serous tissues. Where the processed animal tissue is made from fibro-serous tissues, the tissue can be from the dura mater, pericardium, peritoneum, tunica vaginalis, and dermas. Typically, these tissues are cleansed, dehydrated, cross-linked, and sterilized. Processed animal tissues are preferably chemically cross-linked animal tissues prepared by any of a number of methods that are well known in the art. However, any method of reducing or removing the antigenic sites within the tissue can be used to prepare the animal tissue. Examples of such methods include, but are not limited to, freeze-drying, protease treating, and acid treating the tissue to remove the antigenic sites. Tissues from a patient's own body will not need to undergo these processing steps.

Synthetic polymers include polymers such as polytetrafluoroethylene (PTFE), such as Teflon® (DuPont, Wilmington, Del.); expanded polytetrafluoroethylene (EPTFE), such as Gore-Tex® (W.L. Gore & Associates, Inc., Newark, Del.), polyesters or polyethylene terephthalates, such as Dacron® polyester (DuPont, Wilmington, Del.), and silicone elastomers. Other suitable materials will be apparent to those skilled in the art.

Combinations of synthetic polymers and processed animal tissues can also be used in slings 50, 150, 250 of the present invention. These combinations may include spliced strips having a combination of parts, including parts made of synthetic polymers and of processed animal tissues. Such combinations preferably include animal tissue that is treated so as to cross-link the collagen or otherwise render impotent the commonly antigenic fibers in the animal tissue. An example of such a combination material is collagen-coated ultrafine polyester mesh (CUFP) of the type disclosed by T. Okoski et al., ASAIO Trans., 1989, p. 391.

The sling 250, as shown in FIG. 4, includes an elongated strip of material having variable dimensions, including a thickness, a width 256 and a length 257. The dimensions of the sling 250 can be varied depending on the use of the sling 250. In some embodiments, the length 257 can be greater than the width 256. In other embodiments, the length 257 can be substantially the same or smaller than the width 256. It is desirable for the width 256 to be at least sufficient to comfortably coapt the urethra to the vaginal wall. In one embodiment, the width 257 may be greater than about 0.5 cm, but less than about 4 cm. Other widths include, but are not limited to, 1–3 cm, 1.5–2.5 cm, and 2 cm. The length 257 should be sufficient to encompass at least a portion of the urethra and provide the urethra with sufficient pressure for proper coaptation. Proper coaptation may be accomplished with a length sufficient to encompass the urethra from at least 90° to about 180° of the circumference of the urethra.

Alternatively, the sling 350, as shown in FIG. 5, may be made sufficiently long to be used to secure the sling 350 to the interior vaginal wall without the use of additional sutures. The sling 350 can include a first portion 351, a middle portion 352, and a second portion 353. In this embodiment, the first portion 351 and the second portion 353 can be used as tethers. The middle portion 352 is that area of the sling 350 that is disposed adjacent the urethra. The first portion 351 and second portion 353 can also be used to secure the sling 350 in place. The width of the sling 350 may be the same for the first portion 351, middle portion 352, and second portion 353. However, the width may be different for one or all three portions 351, 352, 353. In FIG. 5, the width of the middle portion 352 is greater than the first portion 351 or second portion 353.

The sling 350 may be a single piece or be made of a plurality of pieces that are joined by any of a number of well known attachment methods, such as securing the attached piece or pieces to the other portions of the sling 350 using sutures 354 as shown in FIG. 5. Other methods include, but are not limited to, gluing, bonding, and heat sealing.

FIG. 6 depicts another embodiment of the surgical device 410. This embodiment includes a pouch 470. The pouch 470 can be used to permit the sling 450 to be handled without damage, maintain a barrier preventing microorganisms from contacting the sling 450, provide handling flexibility, and ensure that the sling 450 is introduced into the opening or pocket in the patient's body in the desired orientation. When the pouch 470 is made of a low friction material, the pouch 470 may also increase the ease of passage of the sling 450 through the opening created by the dilator 440. The pouch 470 may be made of a variety of materials. Examples of such materials include, but are not limited to, polyvinyls and polyesters such as, polyethylene terephthalate (PET), polyethylene (PE), and ethylene vinyl acetate (EVA). Pouches are also described in copending U.S. patent application Ser. No. 09/023,965 filed Feb. 13, 1998, the entire disclosure of which is incorporated herein by reference.

The pouch 470 can be flat to facilitate delivery of the sling 450 in a flat orientation. However, the pouch 470 may also be conical, or rolled conical, and be provided with means for flattening the sling 450 after delivery. Alternatively, the pouch 470 may be used in conjunction with a sling 450 made from a material that adopts a flat configuration after being delivered into the body.

The pouch 470 can be clear or translucent to permit visualization of the sling 450 within. The pouch 470 can also be made of a porous material such as polyethylene, polyethylene terephthalate, or vinyl made porous by methods well known in the art. Other suitable materials will be apparent to those skilled in the art. The pouch 470 can be adapted to receive a dilator 440 and a sling 450. The surgical device 410 may also include a stiffener 446 as shown in any one of FIGS. 7A–C. FIGS. 7A–C depict three variations of transverse cross-sections of the surgical device 410 along section 7A, 7B, 7C—7A, 7B, 7C of FIG. 6. The stiffener 446 and sling 450 may be housed in the pouch 470 (FIG. 7A). The sling 450 may be housed in the stiffener 446 that is housed in the pouch 470 (FIG. 7B). The sling 450 may be housed in the pouch 470; however, the stiffener 446 is adjacent but not housed in the pouch 470 (FIG. 7C). The length of the pouch 470 may be varied depending upon the length of the sling 450. Alternatively, the pouch 470 may be greater or lesser in length than the sling 450. The pouch 470 is adapted to releasably engage the sling 450.

It is desirable that the sling introduced into the opening in the patient's body be sterile. In this regard, FIG. 8 depicts a further embodiment of the surgical device 510, in which the pouch 570 has pores 572 that can permit rehydration of a sling 550 and/or antibiotic or saline soaks of the sling 550 in the pouch 570 prior to introducing the sling 550 into the patient. The pores 572 may be of any size sufficient to permit wetting of the sling 550. The pores 572 may range in size from about 100 microns to about 0.25 inches. Preferably, the pore size ranges from about 0.01 inches to about 0.15 inches. In one preferred embodiment, the pouch 570 is made of vinyl having a pore size of about 0.125 inches.

Figure 11:
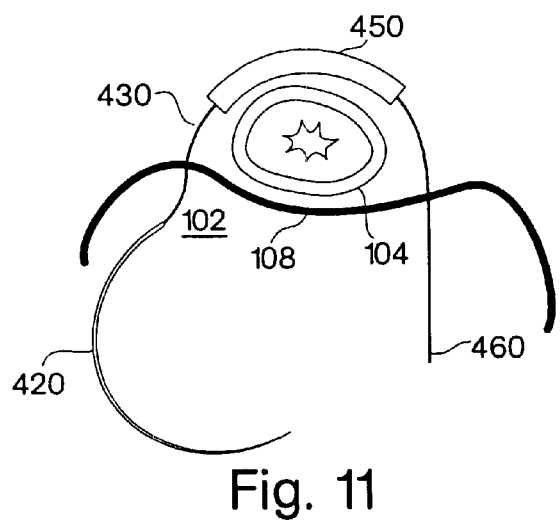
FIG. 11 is a schematic diagram of a step in a method according to one embodiment of the invention.

In another aspect, the invention provides methods for introducing a sling from the vaginal cavity to coapt the urethra to the vaginal wall. One method described below includes the use of a surgical device, as contemplated in the present invention, to coapt the urethra 104, as shown in FIG. 11. While the procedure is described with particular reference to the surgical device 410 of FIG. 6, those skilled in the art will appreciate that any of the surgical devices contemplated herein may be used in this procedure.

In one method according to the present invention, a curved needle 420 such as a Mayo needle is advanced from the vaginal cavity 102, through the anterior portion 108 of the vaginal wall, to pass to one side of the urethra 104. The needle 420 is advanced around the urethra 104 to the other side of the urethra 104 until the needle 420 emerges from the anterior portion of the vaginal wall 108 back into the vaginal cavity 102.

Attached to the needle 420 is a dilator 440 that enlarges the puncture site created by the needle 420. The dilator 440 can increase the area of the puncture site until the opening is sufficiently large to accommodate the sling 450. The dilator 440 is passed about the urethra 104 until it emerges through the anterior vaginal wall 108. The dilator 440 may contain markings 448 along its length to inform the user of the position of the sling 450 in the body. The length of the dilator 440 can permit grasping with a forceps and/or enable pushing the dilator 440 while maintaining tension on the first tether 430 to guide it about the urethra 104. As the needle 420 and dilator 440 are passed through the body, the needle 420 and dilator 440 create a path along the longitudinal axis of the urethra to 104 for the sling 450 to follow.

As the dilator 440 is withdrawn from the body into the vaginal cavity 102, the appropriate marking(s) 448 can be used to alert the user to secure the second tether 460 to the anterior portion of the vaginal wall 108 to prevent further passage of the sling 450 and maintain its position above the anterior portion of the urethra 104. The dilator 440 is then withdrawn from the body along with the pouch 470. The sling 450 is thereby disposed axially to the urethra 104. The first tether 430 is used to secure the sling 450 with enough tension to pull the urethra 104 against the vaginal wall 108 to thereby provide proper coaptation to the urethra 104.

Alternatively, the needle 420, the dilator 440, and pouch 470 may be removed from the body without first securing the second tether 460. In this method, the physician will see two incisions (one on either side of the urethra 104) on the vaginal wall 108 and each incision having a tether 430, 460 emerging from the incision. When the tether 430, 460 is a suture, the tether 430, 460 can be attached to a Mayo needle and secured to the anterior portion of the vaginal wall 108 approximately centering the sling 450 over the urethra 104. The Mayo needle can then be attached to the other tether 430, 460 to repeat the process. A cystoscope can be placed within the urethra 104 to view the interior of the urethra 104. Under visualization, the second suture 460 can be tightened to coapt the urethra 104 and then secured to the anterior portion of the vaginal wall 108.

A device other than sutures may secure the sling 450. The securing device can include, but is not limited to, a fastener, a clip, a staple, or a clamp. The tethers 430, 460 may also be fastened to each other to secure the sling 450. In sutureless embodiments, the sling 450 may be attached directly to the anterior portion of the vaginal wall 108 by a securing device.

In another method according to the invention, an opening or pocket around the urethra 104 is created to receive the sling 450. This opening or pocket can be created prior to passing the surgical device 410 through the body. The opening or pocket may be created in a variety of ways. For example, the opening may be created by hydrodissection in which a bolus of saline or other sterile solution can be injected through the anterior portion of the vaginal wall 108 targeting the tissue that surrounds the urethra 104. For this procedure, the opening or pocket to be created is made to the anterior portion of the urethra 104. An advantage of hydrodissection is that the urethra 104 is separated from the surrounding tissue along tissue planes to create an opening or pocket to receive the sling 450.

Typically, in hydrodissection procedures the volume of saline injected into the tissue is too large to be readily absorbed and, therefore, the tissue must separate to accommodate the saline bolus. Preferably, the volume of saline introduced into the tissue is from about 4 cc to about 10 cc. More preferably, the volume of saline is from about 4 cc to about 5 cc. Multiple injections may be required to create an opening or pocket of sufficient size.

In an alternative approach, the opening or pocket can be created by balloon dissection in which a non-inflated, expandable balloon is introduced into the tissue between the anterior portion of the urethra 104 and the surrounding tissue. When the balloon is expanded, the surrounding tissue is dilated or torn, generating an opening or pocket of sufficient size to receive the sling 450.

In yet another approach, the opening or pocket can be created by dissecting the tissue between the anterior portion of the urethra 104 and the surrounding tissue with blunt dissectors and/or sharp cutters to accommodate the sling 450.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A surgical device for treating urinary incontinence, comprising:
   a curved needle including a distal end and a proximal end;
   a dilator including a distal end and a proximal end, wherein the distal end of the dilator is coupled to the proximal end of the curved needle;
   a sling including a distal end and a proximal end, wherein the distal end of the sling is coupled to the proximal end of the dilator.

2. The surgical device of claim 1 wherein the curved needle includes a curvature sufficient to allow the needle to enter a body through a vaginal cavity, pass to a side of a urethra, continue over an anterior side of the urethra, and exit the body on an opposite side of the urethra.

3. The surgical device of claim 1 wherein the dilator is substantially flat and triangular in shape.

4. The surgical device of claim 1 wherein the dilator is substantially rectangular and tapered at the distal end.

5. The surgical device of claim 1 wherein the dilator comprises a marking to indicate a location of the sling in a body.

6. The surgical device of claim 1 wherein the sling comprises a material selected from the group consisting of a natural material, a synthetic material, and a combination of a natural material and a synthetic material.

7. The surgical device of claim 1 wherein the sling is about 1 centimeter to about 3 centimeters in width.

8. The surgical device of claim 1 further comprising a tether coupling the curved needle to the dilator, wherein the tether is selected from the group consisting of a wire, a suture, and a portion of the sling.

9. The surgical device of claim 1 wherein the sling includes a first portion, a middle portion, and a second portion, the first portion of the sling being smaller in width than the middle portion of the sling.

10. The surgical device of claim 9 wherein the first portion of the sling couples the sling to the dilator.

11. The surgical device of claim 9 wherein the first portion of the sling couples the dilator to the needle.

12. The surgical device of claim 1 further comprising a pouch attached to the dilator.

13. The surgical device of claim 1 further comprising a pouch releasably attached to the sling.

14. The surgical device of claim 1 further comprising a stiffener to maintain the sling in a generally planar orientation as the sling is passed through a body.

15. A surgical device for treating urinary incontinence comprising:
    a sling including a distal end and a proximal end;
    a first tether including a distal end and a proximal end, wherein the proximal end of the first tether is coupled to the distal end of the sling;
    a second tether including a distal end and a proximal end, wherein the distal end of the second tether is coupled to the proximal end of the sling;
    a curved needle coupled to the distal end of the first tether; and
    a dilator disposed along the first tether between the curved needle and the distal end of the sling.

16. A method of treating urinary incontinence, comprising:
    a) introducing a sling into a body; and
    b) positioning the sling on an anterior side of a urethra to coapt the urethra against a vaginal wall.

17. The method of claim 16 wherein the positioning step comprises positioning the sling to surround less than 360° of the circumference of the urethra.

18. The method of claim 16 wherein the introducing step comprises introducing the sling into the body via a vaginal cavity and through the vaginal wall.

19. The method of claim 16 further comprising the step of separating the anterior of the urethra from surrounding tissue.

20. The method of claim 19 wherein the separating step comprises using hyrodissection or balloon dissection.

21. The method of claim 16 wherein the introducing step comprises:

introducing a surgical device into the body via a vaginal cavity and through a vaginal wall to pass to one side of the urethra, passing the surgical device about the anterior side of the urethra, and removing at least a portion of the surgical device from the body on the other side of the urethra back into the vaginal cavity, wherein the surgical device comprises:
- a curved needle including a distal end and a proximal end;
- a dilator including a distal end and a proximal end, wherein the distal end of the dilator is coupled to the proximal end of the curved needle; and
- a sling including a distal end and a proximal end, wherein the distal end of the sling is coupled to the proximal end of the dilator.

22. A method of treating urinary incontinence comprising the steps of:

a) introducing a surgical device into a body via a vaginal cavity, the surgical device comprising:
- a sling including a distal end and a proximal end;
- a first tether including a distal end and a proximal end, wherein the proximal end of the first tether is coupled to a distal end of the sling;
- a second tether including a distal end and a proximal end, wherein the distal end of the second tether is coupled to a proximal end of the sling;
- a curved needle coupled to the distal end of the first tether; and
- a dilator disposed along the first tether between the curved needle and the distal end of the sling;

b) passing the curved needle into the body via the vaginal cavity, through a vaginal wall to one side of a urethra, over an anterior portion of the urethra, and out of the body on the other side of the urethra into the vaginal cavity creating a path for the first tether, the dilator, the sling, and the second tether to follow;

c) advancing the dilator along the path to position the sling about the urethra and leaving at least a portion of the second tether in the vaginal cavity;

d) removing the dilator and at least a portion of the first tether from the body into the vaginal cavity and positioning the sling about the anterior portion of the urethra to coapt the urethra against an anterior portion of the vaginal wall; and e) securing the first tether and second tether to an interior wall of the vaginal cavity.

23. The method of claim 22 further comprising separating the anterior portion of the urethra from surrounding tissue.

* * * * *